United States Patent [19]

Feist et al.

[11] Patent Number: 5,405,991
[45] Date of Patent: Apr. 11, 1995

[54] PROCESS FOR PRODUCING CARBOXYLIC ACID ESTERS FROM CARBOXYLIC ACID HALIDES AND ALCOHOLS

[76] Inventors: Heinz-Rudi Feist, 2 Georgetown-North, Greenwich, Conn. 06831; Wilhelm Pohlmeyer, Harenbergerstrasse 177,, D-30453 Hanover, Germany; Joachim Frehse, Breithauptstrasse 2, D-30625 Hanover, Germany; Werner Rudolph, Oderstrasse 38, D-30559 Hanover, Germany; Max Braun, Varloh 8, D-30900 Wedemark, Germany; Kerstin Eichholz, Im Koellingamoor 38, D-30855 Langenhagen, Germany

[21] Appl. No.: 233,623

[22] Filed: Apr. 26, 1994

[30] Foreign Application Priority Data

Apr. 27, 1993 [DE] Germany ............ 43 13 791.1
Mar. 3, 1994 [DE] Germany ............ 44 06 997.9

[51] Int. Cl.$^6$ ............................................. C07C 67/00
[52] U.S. Cl. ...................................................... 560/239
[58] Field of Search ........................................ 560/239

[56] References Cited

U.S. PATENT DOCUMENTS

| | | | |
|---|---|---|---|
| 3,910,957 | 10/1975 | Pfister et al. | 549/393 |
| 4,351,940 | 9/1982 | Hess et al. | 544/293 |
| 4,513,124 | 4/1985 | Hoffman | 525/452 |
| 5,006,563 | 4/1991 | Hamer et al. | 514/646 |
| 5,189,041 | 2/1993 | Berger et al. | 514/288 |
| 5,262,085 | 11/1993 | Bartmann et al. | 252/299.63 |

FOREIGN PATENT DOCUMENTS 4023106 1/1992 Germany.

OTHER PUBLICATIONS

Kitazume et al., *J. Fluorine Chem.*, 56:271–84 (1992).
Begue et al., *J. Org. Chem.*, 57:3807–14 (1992).
Houben-Weyl, *Methoden der Organischen Chemie*, vol. 8, pp. 543–547 (1952).

*Primary Examiner*—Arthur C. Prescott
*Attorney, Agent, or Firm*—Pro-Techtor International

[57] ABSTRACT

A process for preparing carboxylic esters from carboxylic acid halides or carboxylic anhydrides by reacting one of these starting materials with an alcohol under the catalytic action of "onium" or metal salts of carboxylic acids to obtain high yields of products in anhydrous form in a technically simple manner. The process is especially well suited for preparing 1,1,1-trifluoroethyl trifluoroacetate.

14 Claims, No Drawings

PROCESS FOR PRODUCING CARBOXYLIC ACID ESTERS FROM CARBOXYLIC ACID HALIDES AND ALCOHOLS

BACKGROUND OF THE INVENTION

This invention relates to a process for the catalytic preparation of carboxylic esters from carboxylic acid halides and alcohols.

Many esters of carboxylic acids are used in industry as such. Ethyl acetate and other carboxylic esters are used, for example, as solvents or cleaning agents. Other esters, for example of succinic acid, are used for aromatization. Ethyl trifluoroacetate is, for example, a solvent for the chlorination of paraffins or the polymerization of olefin oxides. Many carboxylic esters are also intermediates in chemical synthesis. Methyl trifluoroacetate and 1,1,1-trifluoroethyl trifluoroacetate yield trifluoroethanol (with or without methanol) on hydrogenation. Trifluoroethanol is used as a solvent and as an intermediate, for example in the preparation of the solvent and anaesthetic isofluraneo Esters of trifluoroacetic acid are also used for the introduction or for the preparation of biologically active compounds which contain a $CF_3$ group. For example, peptides having hormonal activity can be prepared by N-acylation with methyl trifluoroacetate. The trifluoroethyl ester gives shift reagents for NMR analysis on reaction with camphor derivatives. On undergoing the Fries rearrangement with aluminum chloride, phenyl trifluoroacetate gives the corresponding trifluoroacetylated phenol, which is a synthetic building block for pharmaceuticals. Many further applications of esters are known to those skilled in the art, for example the reaction of esters with amines to give amides which are synthetic building blocks #or pharmaceuticals, photosensitizers and dyes.

Esters of chlorodifluoroacetic acid are likewise building blocks for chemical syntheses. For example, the ethyl ester is used in the manufacture of liquid crystals, see DE-OS 4,023,106; and in the preparation of pharmaceuticals, see U.S. Pat. No. 5,006,563. The methyl ester likewise is used for the manufacture of liquid crystals; as a starting compound for microbial production of entantiomeric (asymmetric) secondary alcohols, see T. Kitazume et al., *J. Fluorine Chem.* 56:271-84 (1992); or for the production of fluorinated enolethers in the Wittig synthesis, see J. P. Beque et al., *J. Org. Chem.*, 57:3807 ff. (1992). The esters of chlorodifluoroacetic acid are also precursors for difluorocarbenes.

The preparation of carboxylic esters is conventionally carried out by reaction of the corresponding alcohols with the carboxylic acids under acid catalysis. In this method, the resulting water of reaction must be removed to displace the equilibrium. In the case of fluorinated derivatives this can lead to difficulties because of the preferential binding of water (at the carbonyl functions as hydrates). It is also known that carboxylic esters can be prepared from carboxylic acid chlorides and alcohols under base catalysis. However, this requires a hydrolyric workup, and waste salts are also formed, for example pyridine hydrochloride, which have to be disposed of. The reaction of carboxylic acid halides with alcohols in the absence of base catalysis proceeds at a low reaction rate.

SUMMARY OF THE INVENTION

It is an object of the present invention to provide an improved process for preparing an ester of a carboxylic acid.

Another object of the invention is to provide a process for preparing an ester of a carboxylic acid which is technically simple to carry out.

A further object of the invention is to provide a process for preparing an ester of a carboxylic acid which produces high yields of the desired ester product.

Yet another object of the invention is to provide a process for preparing an ester of a carboxylic acid which does not require hydrolyric work-up or removal of water of reaction.

These and other objects of the invention are achieved by providing a process for preparing a carboxylate ester comprising the step of reacting a starting material selected from the group consisting of carboxylic acid chlorides and carboxylic acid bromides with an alcohol in an anhydrous medium in the presence of a catalytically effective amount of a catalyst selected from the group consisting of alkali metal salts and "onium" salts of a carboxylic acid corresponding to the starting material.

DETAILED DESCRIPTION OF PREFERRED EMBODIMENTS

The process of the invention for preparing carboxylic esters from carboxylic acid chlorides or carboxylic acid bromides and alcohols is characterized in that the reaction is carried out in anhydrous medium in the presence of an alkali metal or "onium" salt of the carboxylic acid corresponding to the carboxylic acid chloride or carboxylic acid bromide used. The resulting carboxylate ester can be isolated, e.g. via distillation.

An addition of acid, for example a carboxylic acid, is not necessary and is preferably not carried out.

It is preferred to start from carboxylic acid chlorides. The catalyst used is preferably an "onium" salt of the carboxylic acid.

The process of the invention can be used, in principle, for the preparation of any esters of any carboxylic acids with any alcohols. In a preferred embodiment a carboxylic acid chloride of the formula

$$R^1C(O)Cl \quad (I)$$

is used, where $R^1$ is alkyl having from 1 to 6 carbon atoms; alkyl substituted by at least 1 halogen atom and having from 1 to 6 carbon atoms; phenyl or tolyl; or phenyl or tolyl substituted by at least 1 halogen atom.

Furthermore, it is preferred to use an alcohol corresponding to the formula

$$R^2OH \quad (II)$$

is used, where $R^2$ is alkyl or alkenyl having from 1 to 8 carbon atoms; alkyl or alkenyl substituted by at least one halogen atom and having from 1 to 8 carbon atoms; phenyl, tolyl or benzyl; or phenyl, tolyl or benzyl substituted by at least one halogen atom and/or at least one nitro group.

It is very particularly preferred that $R^1$ be alkyl substituted by at least one fluorine atom and having from 1 to 4 carbon atoms, and that $R^2$ be alkyl or alkenyl having from 1 to 4 carbon atoms; alkyl or alkenyl substituted by at least one halogen atom and having from 1 to 4 carbon atoms; phenyl; or phenyl substituted by at least 1 halogen atom and/or by at least one nitro group. In particular, $R^1$ may be perfluoromethyl, perfluoroethyl, perfluoropropyl, or chlorodifluoromethyl. Particularly preferably $R^2$ is alkyl or alkenyl having from 1 to 3 carbon atoms; alkyl or alkenyl substituted by at least one fluorine atom and having from 1 to 3 carbon atoms; phenyl; or phenyl substituted by at least one fluorine atom and/or at least one nitro group.

Suitable alkali metal salts of carboxylic acids include, for example, potassium and sodium salts.

As used herein, the term "onium" denotes cations containing positively charged nitrogen, for example protonated aromatic nitrogen bases such as pyridinium or protonated alkyl-, dialkyl- or trialkyl-ammonium cations having up to 20 carbon atoms, or denotes cycloalkyl-substituted ammonium compounds or cycloaliphatic nitrogen bases such as piperidinium or quaternary ammonium cations.

Carboxylic acid salts which are especially suitable include "onium" salts in which "onium" is a nitrogen cation of the formula $R^I R^{II} R^{III} R^{IV} N^+$, where $R^I$, $R^{II}$, $R^{III}$ and $R^{IV}$ are, independently of one another, hydrogen, alkyl having from 1 to 20 carbon atoms, aryl or aralkyl, or where $R^I$ and $R^{II}$ or where $R^{III}$ and $R^{IV}$, or where $R^I$, $R^{II}$ and $R^{III}$ or where $R^I$, $R^{II}$, $R^{III}$ and $R^{IV}$ form saturated or unsaturated ring systems, optionally with inclusion of the nitrogen atom. In this context the term "aryl" refers in particular to phenyl or phenyl substituted by one or more C1-C2-alkyl groups. Salts which are especially suitable include those in which "onium" is ammonium, pyridinium or $R^{1'} R^{2'} R^{3'} R^{4'} N^+$ where $R^{1'}$, $R^{2'}$, $R^{3'}$ and $R^{4'}$ are, independently of one another, hydrogen, alkyl having from 1 to 15 carbon atoms, phenyl or benzyl. Examples of such cations which may be mentioned include pyridinium, piperidinium, anilinium, benzyltriethylammonium and triethylammonium.

The process is particularly suitable for preparing esters of acetic acid substituted by one or more fluorine atoms. For example, phenyl trifluoroacetate can be prepared by the process of the invention. The process of the invention is especially suitable for preparing esters of chlorodifluoroacetic acid or trifluoroacetic acid with 1,1,1-trifluoroethanol, methanol, ethanol, isopropanol, 4-nitrophenol, pentafluorophenol and allyl alcohol.

The molar ratio of the carboxylic acid halide to the alcohol advantageously lies above 0.9. The alcohol can also be used in a higher excess and serve as a solvent, particularly if it is an alcohol substituted by electronegative groups, for example fluorine atoms. Advantageously, the molar ratio of alcohol to carboxylic acid halide is between 0.9:1 and 1.1:1, or if the alcohol also serves as a solvent, up to 5:1.

The temperature at which the reaction is carried out advantageously lies in the range from ambient temperature (about 20° C.) up to the boiling point of the mixture, for example up to 100° C. The reaction is carried out at ambient pressure (about 1 bar abs.) or else, if desired, at elevated pressure, for example at a pressure of up to 5 bar abs.

The alkali metal or "onium" salt may be present in catalytic or in molar amounts. Advantageously, the molar ratio of acid halide to carboxylate salt lies in the range from 1:1 to 20,000:1.

In one specific embodiment of the invention, the acid chloride or acid bromide and the alkali metal or "onium" salt of the carboxylic acid are generated in situ. For this purpose, the corresponding alkali metal or "onium" halide, preferably the chloride or bromide, especially the chloride, is reacted with the anhydride of the carboxylic acid to be used. In this reaction, the anhydride of the carboxylic acid forms the corresponding acid halide and the corresponding salt. In this embodiment, spent halide catalysts may be employed as the alkali metal or "onium" halide, thereby converting the spent catalyst into a useful product.

It is preferred to use an "onium" salt, in particular a pyridinium or a piperidinium salt, as the catalyst salt.

The invention has the advantage that carboxylate esters can be produced in a technically simple manner without a hydrolytic workup. With most esters there is also no formation of waste products such as pyridine hydrochloride.

Further details of the invention will be apparent from a consideration of the following specific examples, which are merely illustrative, and are not limiting on the scope of the invention.

EXAMPLE 1

Preparation of trifluoroethyl trifluoroacetate by reacting trifluoroacetyl chloride with 2,2,2-trifluoroethanol in the presence of pyridinium trifluoroacetate.

30 g (0.16 mole) of pyridinium trifluoroacetate in 355 g (3.55 mole) of 2,2,2-trifluoroethanol were introduced as an initial charge into a laboratory circulating reactor apparatus (one-liter four-necked flask fitted with KPG stirrer, a Prominent pump, and a 30 cm column packed with Raschig rings), and the initial charge was circulated at an internal temperature of 54° C. 134 g (1.01 mole) of trifluoroacetyl chloride were subsequently metered into the flask via an immersed inlet tube over a period of 100 minutes. After the trifluoroacetyl chloride addition was complete, the mixture was allowed to react for a further 10 minutes. Subsequent fractional distillation of the reaction mixture via a Vigreux column (temperature at the distillation head: from 54° to 56° C.) yielded 177.8 g of trifluoroethyl trifluoroacetate, corresponding to 89.8% of the theoretical yield. The trifluoroethanol/pyridinium salt mixture remaining in the reservoir flask can be used again for esterification with equal effectiveness.

EXAMPLES 2-7

Preparation of trifluoroacetic esters by reaction of trifluoroacetyl chloride with methanol, ethanol, isopropanol, 4-nitrophenol, pentafluorophenol and allyl alcohol in the presence of pyridinium trifluoroacetate.

Following the procedure of Example 1, the corresponding esters were also prepared from trifluoroacetyl chloride and methanol (94%), ethanol (96%), isopropanol (89%), 4-nitrophenol (85%), pentafluorophenol (92%) and allyl alcohol (81%).

EXAMPLE 8

Preparation of trifluoroethyl trifluoroacetate by reaction of trifluoroacetic anhydride with 2,2,2-trifluoroethanol in the presence of pyridinium hydrochloride.

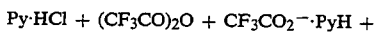

-continued

$$CF_3CO-OCH_2CF_3 + PyTFA + HCl$$

A 250 ml three-neck flask fitted with KPG stirrer, dry-ice condenser and dropping funnel was charged with 23.11 g (0.2 mole) of pyridinium hydrochloride and 20.0 g (0.2 mole) of 2,2,2-trifluoroethanol. Subsequently, at an internal reaction temperature from 52° to 55° C., 42.01 g (0.2 mole) of trifluoroacetic anhydride were added dropwise over a period 3 hours. The yield of trifluoroethyl trifluoroacetate was 98% (GC). The resulting reaction solution was either used as catalyst mixture for experiments as described in Example 1, or 2,2,2-trifluoroethanol was distilled off. During the course of the distillation the trifluoroacetic acid, which initially formed in the reaction, reacted in the distillation flask with the pyridinium hydrochloride to form pyridinium trifluoroacetate and HCl.

EXAMPLE 9

Preparation of methyl chlorodifluoroacetate.

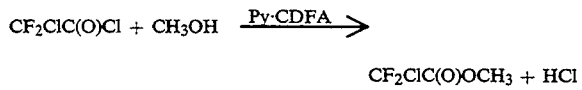

$$CF_2ClC(O)OCH_3 + HCl$$

Preparation of pyridinium chlorodifluoroacetate:

7.91 g (0.10 mole) of pyridine were initially introduced under a $N_2$ atmosphere into a 250 ml three-necked flask equipped with a dripping funnel, a KPG-stirrer and a 40 cm packed column, and 13.05 g (0.10 mole) chlorodifluoroacetic acid were slowly added dropwise with rapid stirring (and with spontaneous heating).

Preparation of the ester:

The resulting pyridinium salt was taken up in 32.0 g (1.0 mole) of methanol (the salt dissolved immediately). After heating in an oil bath to 50° C., 148.9 g (1.0 mole) chlorodifluoroacetyl chloride were added dropwise with vigorous development of HCl. A gas chromatographic (GC) analysis of the reaction mixture after completion of the dropwise addition indicated that the acid chloride had been quantitatively converted to the ester. The resulting clear yellow solution was subsequently subjected to fine distillation over the 40 cm packed column. At a bottoms temperature of 80°–85° C. and a head temperature of 78°–79° C., methyl chlorodifluoroacetate was obtained in 99% purity.

EXAMPLE 10

Preparation of ethyl chlorodifluoroacetate.

Ethyl chlorodifluoroacetate was produced in a manner analogous to Example 9. 10 mole-% pyridinium chlorodifluoroacetate catalyst, 46.06 g (1.0 mole) ethanol and 148.9 g (1.0 mole) chlorodifluoroacetyl chloride were used. After addition of 0.5 mole of the acid chloride, a strong turbidity (phase formation) was observed in the reaction solution, which upon addition of further acid chloride disappeared again by the end of the reaction. A GC analysis after the evolution of HCl had ended one again showed a quantitative conversion of the acid chloride to the ester. The ester was purified by distillation over the 40 cm packed column under vacuum.

EXAMPLE 11

Preparation of propyl chlorodifluoroacetate.

Propyl chlorodifluoroacetate was prepared in a manner analogous to Example 9. 10 mole-% pyridinium chlorodifluoroacetate catalyst, 60.1 g (1.0 mole) n-propanol and 148.9 g (1.0 mole) chlorodifluoroacetyl chloride were used. During the course of the reaction, the formation of two phases was noted. After the evolution of HCl had ended, stirring was stopped, and the phases were analyzed and characterized by GC-MS. The upper phase contained over 96% of the desired propyl chlorodifluoroacetate in addition to pyridinium salts. The lower phase contained the catalyst salt as its principal component in addition to traces of the product. The conversion of the acid chloride to the ester was quantitative. After separation of the phases, the ester was purified by distillation over the 40 cm packed column under vacuum.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for preparing a carboxylate ester comprising the step of reacting a starting material selected from the group consisting of carboxylic acid chlorides and carboxylic acid bromides with an alcohol in an anhydrous medium in the presence of a catalytically effective amount of a catalyst selected from the group consisting of alkali metal salts and "onium" salts of a carboxylic acid corresponding to the starting material.

2. A process according to claim 1, wherein the reaction is carried out without addition of carboxylic acid.

3. A process according to claim 1, wherein said starting material is a carboxylic acid chloride.

4. A process according to claim 1, wherein said alcohol corresponds to the formula:

$$R^2OH \qquad (II)$$

wherein $R^2$ represents $C_1$–$C_8$ alkyl or alkenyl, $C_1$–$C_8$ alkyl or alkenyl substituted by at least one halogen atom, phenyl, tolyl, benzyl, or phenyl, tolyl or benzyl substituted by at least one substituent selected from the group consisting of halogen and nitro.

5. A process according to claim 1, wherein said starting material is a carboxylic acid chloride corresponding to the formula $$R^1C(O)Cl \qquad (I)$$

wherein $R^1$ represents $C_1$–$C_6$ alkyl, $C_1$–$C_6$ alkyl substituted by at least one halogen atom, phenyl, tolyl, or phenyl or tolyl substituted by at least 1 halogen atom.

6. A process according to claim 5, wherein $R^1$ represents $C_1$–$C_4$ alkyl substituted by at least 1 fluorine atom, and said alcohol corresponds to the formula $R_2OH$ wherein $R^2$ represents $C_1$–$C_4$ alkyl or alkenyl, $C_1$–$C_4$ alkyl or alkenyl substituted by at least one halogen atom, phenyl or phenyl substituted by at least one substituent selected from the group consisting of halogen and nitro.

7. A process according to claim 6, wherein $R^1$ represents perfluoromethyl, perfluoroethyl, perfluoropropyl, or chlorodifluoromethyl.

8. A process according to claim 6, wherein $R^2$ represents $C_1$–$C_3$ alkyl or alkenyl, $C_1$–$C_3$ alkyl or alkenyl substituted by at least one fluorine atom, phenyl, or phenyl substituted by at least 1 substituent selected from the group consisting of fluorine and nitro.

9. A process according to claim 1, wherein said alcohol is used as a solvent for the reacting step.

10. A process according to claim 1, wherein said starting material and catalyst are present in a molar ratio in the range from 1:1 to 20,000:1.

11. A process according to claim 1, wherein said starting material and said catalyst are generated in situ by reacting an alkali metal chloride or bromide or an "onium" chloride or bromide with a carboxylic acid anhydride.

12. A process according to claim 1, wherein an "onium" salt is used.

13. A process according to claim 12, wherein said "onium" salt is a pyridinium salt or a piperidinium salt.

14. A process according to claim 1, wherein trifluoroacetyl chloride is reacted with an alcohol selected from the group consisting of methanol, ethanol, isopropanol, 4-nitrophenol, pentafluorophenol, allyl alcohol and 1,1,1-trifluoroethanol.

* * * * *

UNITED STATES PATENT AND TRADEMARK OFFICE
CERTIFICATE OF CORRECTION

PATENT NO. : 5,405,991
DATED : April 11, 1995
INVENTOR(S) : Heinz-Rudi FEIST et al.

It is certified that error appears in the above-indentified patent and that said Letters Patent is hereby corrected as shown below:

On title page, change, — Attorney, Agent or Firm of the above-referenced patent from "Pro-Techtor International" to --Evenson, McKeown, Edwards & Lenahan--.

Signed and Sealed this

Eighth Day of August, 1995

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,405,991
DATED : April 11, 1995
INVENTOR(S) : Heinz-Rudi FEIST et al.

It is certified that error appears in the above-identified patent and that said Letters Patent is hereby corrected as shown below:

On the title page, Item [73], insert

-- Name of Assignee: Solvay Fluor und Derivate GmbH
City and Country: Hannover, Germany--.

Signed and Sealed this

Twenty-ninth Day of June, 1999

Attest:

Q. TODD DICKINSON

*Attesting Officer*    *Acting Commissioner of Patents and Trademarks*